United States Patent
Kobayashi et al.

(10) Patent No.: US 10,838,194 B2
(45) Date of Patent: Nov. 17, 2020

(54) OPTICAL TRANSMISSION MODULE AND ENDOSCOPE

(71) Applicant: OLYMPUS CORPORATION, Tokyo (JP)

(72) Inventors: Keiichi Kobayashi, Tatsuno-machi (JP); Youhei Sakai, Ina (JP)

(73) Assignee: OLYMPUS CORPORATION, Tokyo (JP)

( * ) Notice: Subject to any disclaimer, the term of this patent is extended or adjusted under 35 U.S.C. 154(b) by 182 days.

(21) Appl. No.: 16/020,059

(22) Filed: Jun. 27, 2018

(65) Prior Publication Data

US 2018/0307035 A1    Oct. 25, 2018

Related U.S. Application Data

(63) Continuation of application No. PCT/JP2015/086501, filed on Dec. 28, 2015.

(51) Int. Cl.

| | |
|---|---|
| *G02B 6/06* | (2006.01) |
| *G02B 6/04* | (2006.01) |
| *G02B 6/12* | (2006.01) |
| *G02B 6/36* | (2006.01) |
| *G02B 23/24* | (2006.01) |
| *G02B 6/26* | (2006.01) |
| *A61B 1/05* | (2006.01) |
| *A61B 1/00* | (2006.01) |

(52) U.S. Cl.
CPC ........ *G02B 23/2476* (2013.01); *A61B 1/0011* (2013.01); *A61B 1/00013* (2013.01); *A61B 1/05* (2013.01); *G02B 6/262* (2013.01); *G02B 23/2469* (2013.01)

(58) Field of Classification Search
CPC .............. G02B 23/2476; G02B 6/262; G02B 23/2469; G02B 6/4232; G02B 6/424; G02B 6/4202; A61B 1/05; A61B 1/00013; A61B 1/0011
USPC ...... 385/60, 62–66, 88, 91, 92, 94, 117, 119
See application file for complete search history.

(56) References Cited

U.S. PATENT DOCUMENTS

| | | | |
|---|---|---|---|
| 2006/0098923 A1* | 5/2006 | Fujiwara | G02B 6/4292 385/88 |
| 2010/0148041 A1* | 6/2010 | Takamatsu | G02B 6/4203 250/227.24 |
| 2012/0237158 A1 | 9/2012 | Inoue et al. | |

FOREIGN PATENT DOCUMENTS

| | | |
|---|---|---|
| JP | S63040495 U1 | 3/1988 |
| JP | H04308804 A | 10/1992 |

(Continued)

OTHER PUBLICATIONS

International Search Report dated Mar. 29, 2016 issued in PCT/JP2015/086501.

*Primary Examiner* — Kaveh C Kianni
*Assistant Examiner* — Hung Q Lam
(74) *Attorney, Agent, or Firm* — Scully, Scott, Murphy & Presser, P.C.

(57) ABSTRACT

An optical transmission module includes: an optical fiber a cross section of which has a circular shape and an end surface of which is an inclined surface; and an optical element part including an optical element, wherein a cutout surface extending in an optical axis direction is formed in an outer circumference of an end portion of the optical fiber, and the angle of the inclined surface with respect to the main surface of the optical element is defined by the cutout surface, such that light guided through the optical fiber is optically coupled to the optical element.

12 Claims, 12 Drawing Sheets

(56) References Cited

FOREIGN PATENT DOCUMENTS

| | | |
|---|---|---|
| JP | H109186348 A | 7/1997 |
| JP | H110325917 A | 12/1998 |
| JP | H111026783 A | 1/1999 |
| JP | 2004325675 A | 11/2004 |
| JP | 2006065032 A | 3/2006 |
| JP | 2007264411 A | 10/2007 |
| JP | 2012194401 A | 10/2012 |
| JP | 2015104387 A | 6/2015 |
| WO | 2015079780 A1 | 6/2015 |

* cited by examiner

OPTICAL TRANSMISSION MODULE AND ENDOSCOPE

CROSS REFERENCE TO RELATED APPLICATION

This application is a continuation application of PCT/JP2015/086501 filed on Dec. 28, 2015, the entire contents of which are incorporated herein by this reference.

BACKGROUND OF INVENTION

1. Field of the Invention

The present invention relates to an optical transmission module including an optical element and an optical fiber through which an optical signal from the optical element is transmitted, and to an endoscope including the optical transmission module.

2. Description of the Related Art

An endoscope includes an image pickup device such as a CCD at a rigid distal end portion of an insertion section. Use of a high-pixel image pickup device for an endoscope has been recently considered. When a high-pixel image pickup device is used, a signal amount transmitted from the image pickup device to a signal processing device (a processor) is increased. Accordingly, optical signal transmission using an optical transmission module via a thin optical fiber by means of an optical signal is preferable to electrical signal transmission via metallic wiring by means of an electrical signal.

Since the invasiveness of an optical transmission module provided in a rigid distal end portion of an endoscope is low, to downsize such an optical transmission module, particularly reducing a diameter of the optical transmission module is an important issue.

An optical transmission module for an endoscope disclosed in Japanese Patent Application Laid-Open Publication No. 2015-104387 includes an optical element, a wiring board, a holding member (a ferrule), and an optical fiber. In the optical transmission module, the optical element, the wiring board, and the holding member are arranged side by side in the thickness direction of the optical element.

On the other hand, the diameter of the optical transmission module can be reduced by having an end surface of the optical fiber inclined. For example, Japanese Patent Application Laid-Open Publication No. 10-325917 discloses an optical reception device in which an end surface of an optical fiber is an inclined surface, and light reflected by the inclined surface is received by a light receiving element.

SUMMARY OF THE INVENTION

An optical transmission module of an embodiment according to the present invention includes: an optical fiber a cross section of which has a circular shape and an end surface of which is an inclined surface; and an optical element part including an optical element that is a light emitting element having a light emitting surface as a main surface or a light receiving element having a light receiving surface as a main surface, wherein a cutout surface extending in an optical axis direction is formed in an outer circumference of an end portion of the optical fiber, and an angle of the inclined surface with respect to the main surface of the optical element is defined by the cutout surface, such that light guided through the optical fiber is optically coupled to the optical element.

An endoscope according to another embodiment according to the present invention includes an optical transmission module at a rigid distal end portion of an insertion section, wherein the optical transmission module includes: an optical fiber a cross section of which has a circular shape and an end surface of which is an inclined surface; and an optical element part including an optical element that is a light emitting element having a light emitting surface as a main surface or a light receiving element having a light receiving surface as a main surface, wherein a cutout surface extending in an optical axis direction is formed in an outer circumference of an end portion of the optical fiber, and an angle of the inclined surface with respect to the main surface of the optical element is defined by the cutout surface, such that light guided through the optical fiber is optically coupled to the optical element.

DETAILED DESCRIPTION OF THE PREFERRED EMBODIMENTS

First Embodiment

Figure 1:
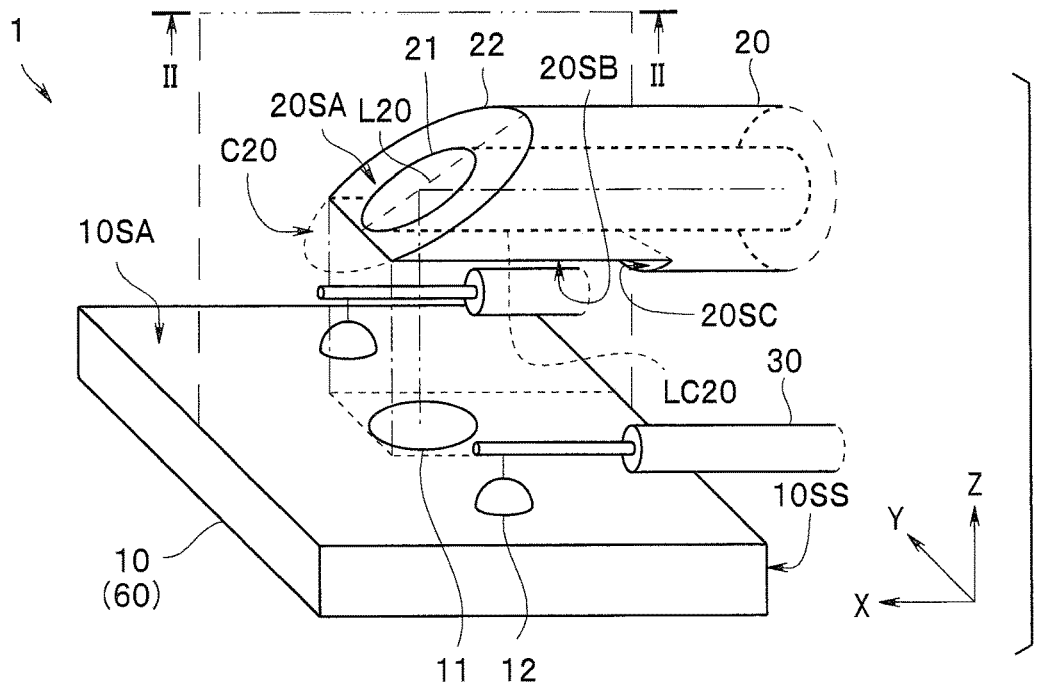
FIG. 1 is an exploded view of an optical transmission module of a first embodiment.
Figure 2:
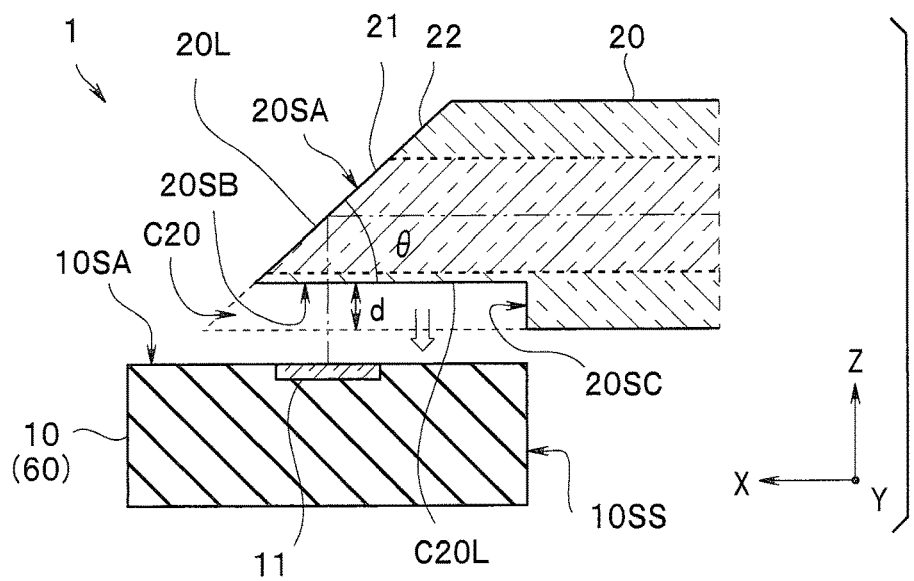
FIG. 2 is a cross-sectional view of the optical transmission module of the first embodiment, taken along line II-II in FIG. 1.

As illustrated in FIG. 1 and FIG. 2, an optical transmission module 1 of the present embodiment includes an optical element 10 as an optical element part 60, an optical fiber 20, and a cable 30.

Note that all the drawings are schematic views in which the relationship between the thickness and the width of each component or the ratio among the thicknesses of the components may be different from an actual relationship or ratio. The mutual relationship or ratio of the component dimensions may vary in the drawings. Illustration of the components may also be partially omitted. Note that, in FIG. 1 and the like, the left side, i.e., the direction of a distal end of the optical fiber 20 (an X-axis value increase direction) is referred to as the "front side", and the direction of the optical fiber 20 toward the optical element 10, i.e., a Z-axis value increase direction is referred to as the "upper side".

For example, the optical element 10 is a VCSEL (vertical cavity surface emitting laser) light emitting element including a light emitting unit 11 that outputs light of an optical signal to a light emitting surface 10SA, which is a main surface. For example, the optical element 10 which is very compact with the dimensions of 250 μm×300 μm in plan view includes, on the light emitting surface 10SA, the light emitting unit 11 having a diameter of 20 μm and a bonding bump 12 for supplying a driving signal to the light emitting unit 11. The cable 30 is bonded to the bonding bump 12 on the optical element 10. The optical element 10 emits light in a direction orthogonal to the light emitting surface 10SA.

The bonding bump 12 has a height of 10 to 100 μm, and is a stud bump, a plated bump, a ball bump, or the like, made of gold or solder, for example.

The optical fiber 20 a cross section of which is a circular shape is an MMF (multi mode fiber) of which alignment can be easily performed, for example. A core 21 through which light is transmitted has a diameter of 50 μm. A clad 22 covering the outer circumference of the core 21 has a diameter of 125 μm. For example, the core 21 has a refractive index of 1.50 to 1.60, which is larger than the refractive index of the clad 22 by at least 0.01.

The cross section of the optical fiber 20 has a circular shape, while an end surface of the optical fiber 20 has been processed into an inclined surface 20SA. Further, the outer circumference of the end portion of the optical fiber 20 has been processed to have a cutout C20 having a rectangular cutout surface 20SB that extends in the optical axis direction. The cutout C20 is formed such that the center line LC20 of the cutout C20 parallel with the optical axis direction of the cutout surface 20SB intersects with the longitudinal axis L20 of the inclined surface 20SA. A rear end wall surface 20SC of the cutout C20 is formed so as to be perpendicular to the cutout surface 20SB.

The optical fiber 20 is attached in a state where the cutout surface 20SB is in contact with the main surface 10SA of the optical element 10. Accordingly, the angle θ of the inclined surface 20SA with respect to the main surface 10SA of the optical element 10, that is, the rotation direction of the optical fiber 20 is automatically defined such that light guided through the optical fiber 20 is optically coupled to the optical element 10.

Note that a reflection film may be provided on the inclined surface 20SA. For example, a reflection film made of gold or aluminum, etc., which has high reflectance, may be provided by a sputtering method, so that light can be more efficiently reflected.

In addition, the entirety (including the end portion of the optical fiber 20) of the optical transmission module 1 may be covered with a light-shielding resin. The light-shielding resin prevents leakage of light from the optical element 10, and also improves the reflection efficiency because even the inclined surface 20SA is covered with the light-shielding resin.

The inclined angle θ of the inclined surface 20SA of the optical fiber 20 is defined, as appropriate, in light of the relative position relationship with respect to the optical element 10. For example, when the inclined angle is 45 degrees, light emitted from the light emitting unit 11 of the optical element 10 in the direction orthogonal to the light emitting surface 10SA is bent at 90 degrees by the inclined surface 20SA. With the inclined angle θ of 35 to 55 degrees, light can be efficiently guided to the core 21 of the optical fiber 20.

In a conventional optical transmission module in which an end surface of an optical fiber is formed into an inclined surface, the angle formed between a main surface of an optical element and the inclined surface of the optical fiber, that is, the rotation direction of the optical fiber needs to be precisely defined. For example, an adjustment process is needed in which, while light is actually being guided to the optical fiber, the optical fiber is rotated, a rotation angle at which the amount of light becomes the largest is found out, and the optical fiber is fixed at the rotation angle. An optical transmission module in which an end surface of an optical fiber is formed into an inclined surface involves a complicated adjustment process, and thus, there is a possibility that such an optical transmission module cannot be easily manufactured. In addition, when an optical fiber is fixed, not only the rotation direction but also the position of the optical fiber with respective to an optical element needs to be adjusted in an in-plane direction.

In contrast, in the optical transmission module 1, the rotation direction of the optical fiber 20 with respect to the optical element 10 is automatically defined. Therefore, no complicated adjustment process is necessary so that the optical transmission module 1 can be easily manufactured.

Moreover, since the optical fiber 20 includes the cutout C20, an optical path of the optical transmission module 1 becomes short by the depth d of the cutout C20. For this reason, the optical loss in the optical transmission module 1 is small. Furthermore, the height (the dimension in the Z-direction) of the optical transmission module 1 becomes low by the depth d of the cutout C20, so that the diameter of the optical transmission module 1 is small.

Note that, in order to efficiently guide light to the optical fiber 20, not only the rotation angle θ of the optical fiber 20 but also positioning of the optical fiber 20 in the in-plane direction (the XY-surface direction) with respect to the optical element 10 is important. That is, the center of the inclined surface 20SA of the optical fiber 20 needs to be positioned directly above the light emitting unit 11. As a result of contact of a rear end wall surface 20SC of the cutout C20 with a rear side surface loss of the optical element 10, positioning of the optical fiber 20 is automatically performed in the in-plane direction.

The optical fiber 20 and the optical element 10 are bonded together with an adhesive (not illustrated) made from an ultraviolet curable resin, for example. An adhesive made from a transparent resin having a refractive index equal to the refractive index of the clad 22 of the optical fiber 20 is used when there is a possibility that the adhesive enters a region of the optical path.

Note that the optical element may be a light receiving element such as a photodiode (PD). For example, the optical element formed of a photodiode converts, into an electrical signal, incident light from a direction orthogonal to a light receiving surface as a main surface of the optical element. For example, a light receiving element that is very compact with the dimensions of 350 μm×300 μm in plan view has, on a light receiving surface, a light receiving unit having a diameter of 50 µm and a connection terminal which is electrically connected to the light receiving unit and which outputs a received electrical signal.

It is reasonably understood that even an optical transmission module an optical element of which is a light receiving element has a small diameter and can be easily manufactured, like the optical transmission module 1.

That is, the optical transmission module of the embodiment includes the optical fiber a cross section of which has a circular shape and an end surface of which is the inclined surface, and includes the optical element part including the optical element which is a light emitting element or a light receiving element, the rectangular cutout surface extending in the optical axis direction is formed in the outer circumference of the end portion of the optical fiber, and the optical fiber is attached in the state where the cutout surface is in contact with the main surface of the optical element. As a result, the angle of the inclined surface with respect to the main surface of the optical element, that is, the rotation direction is fixed to an angle at which light guided through the optical fiber is optically coupled to the optical element.

Modification of First Embodiment

Next, optical transmission modules 1A to 1D of first to fourth modifications of the first embodiment are described. The optical transmission modules 1A to 1D are each similar to the optical transmission module 1 and provide the same effect as the effect provided by the optical transmission module 1. Therefore, components having the same functions are denoted by the same reference numerals and an explanation thereof is omitted.

As described above, in the optical transmission module 1, positioning of the optical fiber 20 in the in-plane direction is defined by the rear end wall surface 20SC of the cutout C20. However, there is a possibility that processing of the optical fiber 20 having a precise cutout length and a precise shape of the rear end wall surface 20SC is not easy.

In contrast, in each of the optical transmission modules 1A to 1D, a positioning member with which an end portion of an optical fiber 20A is in contact is provided on the light emitting surface (the main surface) 10SA of the optical element 10. The optical fiber 20A of each of the optical transmission modules 1A to 1D has the cutout C20 longer than the cutout C20 of the optical fiber 20 of the optical transmission module 1. Further, the length, etc. of the cutout C20A does not need to be precisely managed. Therefore, processing of the optical transmission modules 1A to 1D is easy.

First Modification of First Embodiment

Figure 3:
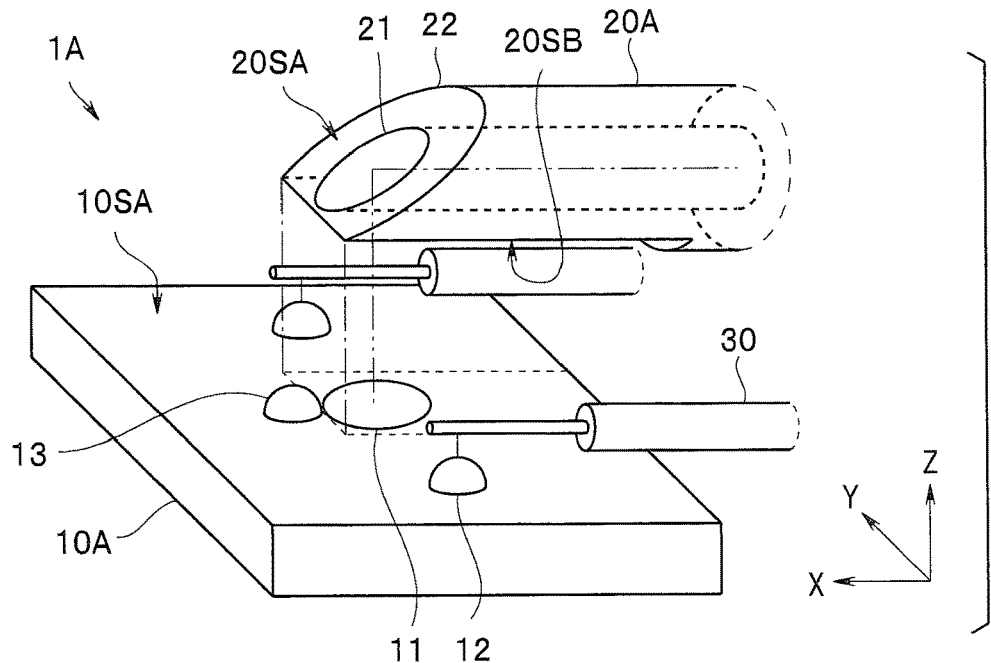
FIG. 3 is an exploded view of an optical transmission module of a first modification of the first embodiment.

As illustrated in FIG. 3, in the optical transmission module 1A of the first modification of the first embodiment, the positioning member is a first bump 13 which is a bump for positioning. That is, as a result of contact of the end portion of the optical fiber 20 with the first bump 13 on the optical element 10A, the position of the optical fiber 20 is automatically defined in the optical axis direction (the X direction).

The configuration of the first bump 13 provided on the light emitting surface 10SA, which is a main surface, is substantially the same as the configuration of the bonding bump 12. That is, the first bump 13 has a height of 10 to 100 µm, and is a stud bump, a plated bump, or a ball bump, made of gold or solder, for example.

Since the configuration of the first bump 13 is substantially the same as the configuration of the bonding bump 12, the first bump 13 can be provided simultaneously with the time of production of the optical element 10A by substantially the same process. In addition, for example, the bonding bump 12 and the first bump 13 on the optical element 10A are arranged at precise positions by a photolithography method when being in a wafer state.

Note that, when the height of the bonding bump 12 is low, the first bump 13 may be formed of a two-tier bump. For example, at an arrangement position for the first bump 13, a bump having the same configuration as the configuration of the bonding bump 12 is provided, and, on the bump, an additional bump is provided, so that the first bump 13 having a high height can be easily produced at a predetermined position.

The optical transmission module 1A can be more easily manufactured than the optical transmission module 1.

Note that a plurality of the first bumps 13 with which the end portion of the optical fiber 20A is in contact may be arrayed on the optical element 10A. Positioning of the optical fiber 20A the end portion of which is in contact with the plurality of first bumps 13 is also automatically performed in the direction (the Y direction) orthogonal to the optical axis.

Second Modification of First Embodiment

Figure 4:
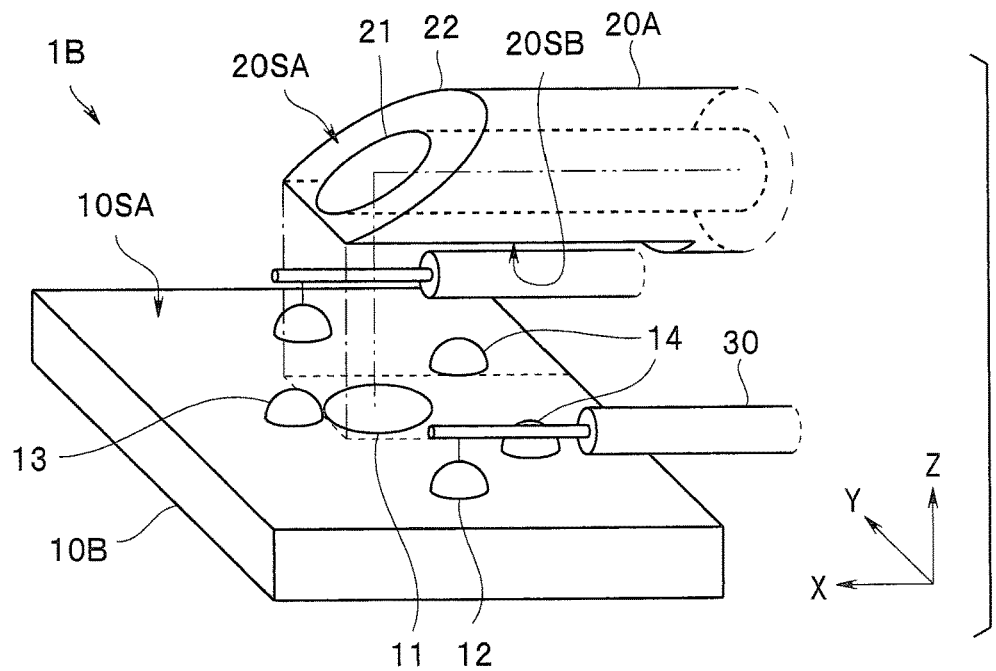
FIG. 4 is an exploded view of an optical transmission module of a second modification of the first embodiment.

As illustrated in FIG. 4, in the optical transmission module 1B of the second modification of the first embodiment, an optical element 10B further includes, on the light emitting surface 10SA which is a main surface, a second bump 14 that is a bump for positioning in the direction orthogonal to the optical axis and is in contact with a side surface of the optical fiber 20A, in addition to the first bump 13 that is a bump for positioning in the optical axis direction and is in contact with the end portion of the optical fiber 20A.

The configuration of the second bump 14 is the same as the configuration of each of the bonding bump 12 and the first bump 13. That is, the second bump 14 is provided simultaneously with the bonding bump 12 and the first bump 13 by the same process.

Positioning of the optical fiber 20A a side surface of which is in contact with the second bump 14 is also automatically performed in the direction (the Y direction) orthogonal to the optical axis. Therefore, the optical transmission module 1B can be more easily manufactured than the optical transmission module 1 or 1A.

Note that positioning of the optical fiber 20A can be automatically performed in the direction (the Y direction) orthogonal to the optical axis as long as one side surface of the optical fiber 20A is in contact with at least one second bump 14. However, in order to facilitate the positioning, the optical element 10B more preferably includes a plurality of the second bumps 14 in contact with both side surfaces of the optical fiber 20A.

Third Modification of First Embodiment

Figure 5:
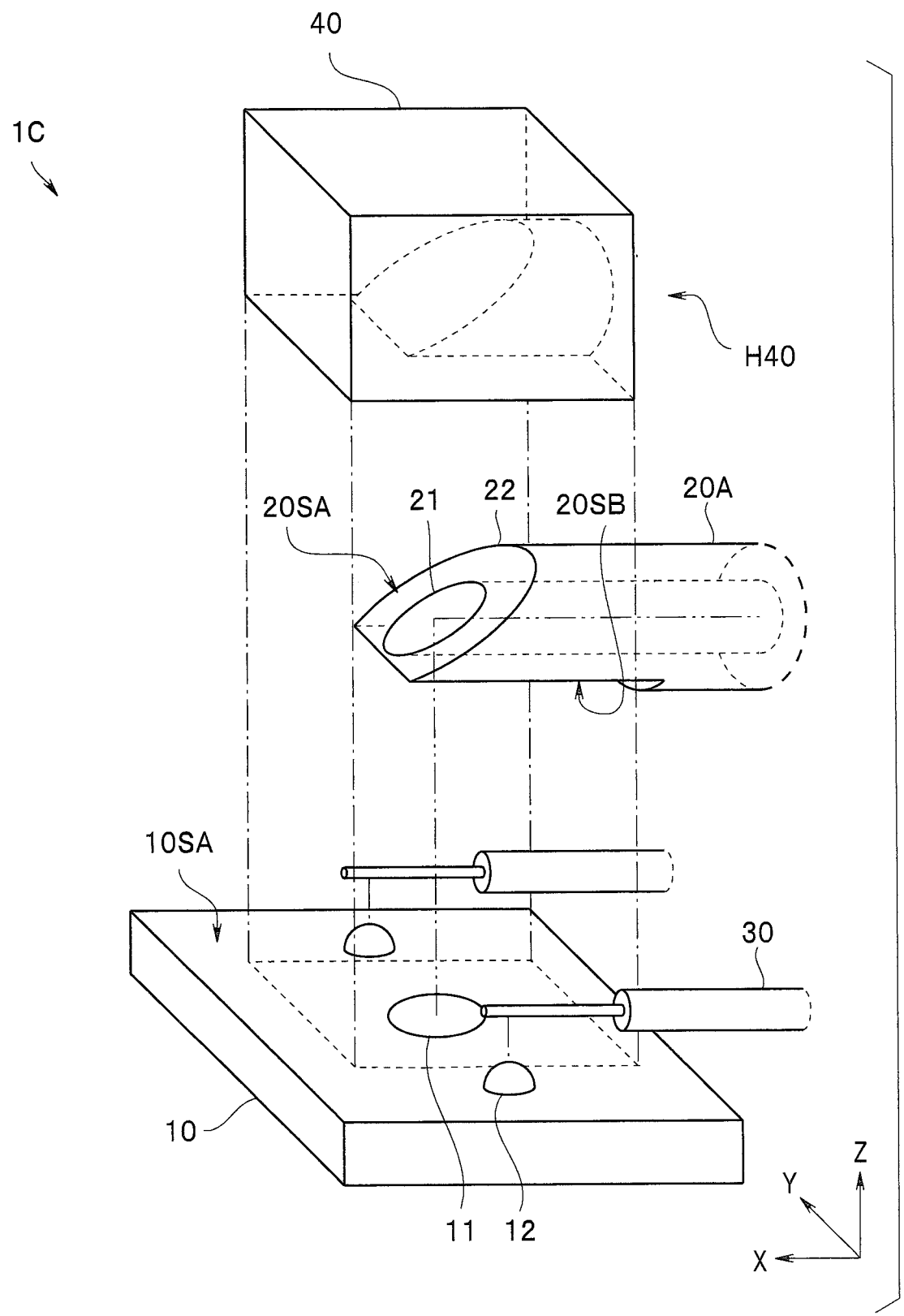
FIG. 5 is an exploded view of an optical transmission module of a third modification of the first embodiment.

As illustrated in FIG. 5, in the optical transmission module 1C of the third modification of the first embodiment, a positioning member 40 provided on the light emitting surface (the main surface) 10SA of the optical element 10 includes a recessed portion H40 in which the end portion of the optical fiber 20A is inserted and fitted.

The positioning member 40 is made from ceramics, Si (silicon), glass, resin, or metal, for example. Note that the recessed portion H40 has a groove-like shape having an opening in the bottom surface of the positioning member 40. The inner dimension of the recessed portion H40 is substantially equal to the outer dimension of the optical fiber 20A to be inserted in the recessed portion H40. Here, the expression "substantially equal" means that the both dimensions have substantially the "same" size to allow the contact state between the outer circumferential surface of the optical fiber 20A and the wall surface of the recessed portion H40. For example, the recessed portion H40 is produced so as to have an inner dimension larger than the outer dimension of the optical fiber 20A by 1 to 5 µm.

As a result of contact of the cutout surface 20SB with the light emitting surface 10SA of the optical element 10, the rotation direction of the optical fiber 20A is automatically defined. As a result of fitting of the end portion of the optical fiber 20A in the recessed portion H40 of the positioning member 40, positioning of the optical fiber 20A is automatically performed in the in-plane direction (the XY direction).

Therefore, the optical transmission module 1C can be more easily manufactured than the optical transmission module 1.

Note that the first bump 13 or the second bump 14 having been described above, may be used in positioning to attach the positioning member 40 to the optical element 10.

Fourth Modification of First Embodiment

Figure 6:
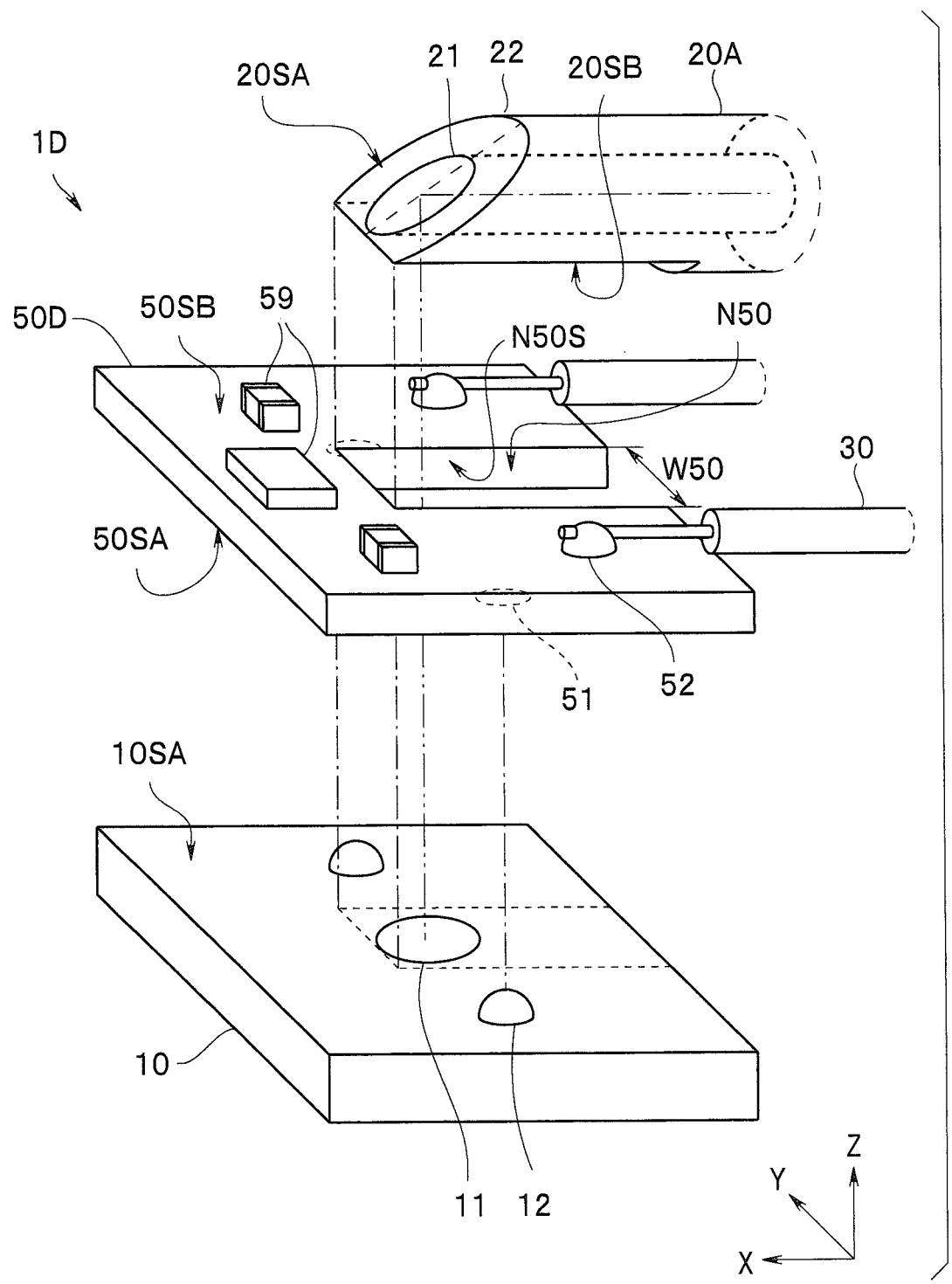
FIG. 6 is an exploded view of an optical transmission module of a fourth modification of the first embodiment.

As illustrated in FIG. 6, in the optical transmission module 1D of the fourth modification of the first embodiment, the positioning member is a wiring board 50 having a first main surface 50SA and a second main surface 50SB opposite to the first main surface 50SA.

A resin substrate, a ceramic substrate, a glass epoxy substrate, a glass substrate, a silicon substrate, or the like is used for a base of the wiring board 50. Note that, from the viewpoint of the downsizing and flexibility, the particularly preferable wiring board 50 is an FPC (flexible printed circuit) substrate having a base of polyimide, etc.

An electrode 51 bonded to the bonding bump 12 of the optical element 10 is provided on the first main surface 50SA of the wiring board 50. A bonding bump 52 which is electrically connected to the bonding bump 12 via through wiring (not illustrated), etc. is provided on the second main surface 50SB. The cable 30 is bonded to the bonding bump 52 on the wiring board 50.

Note that an area between the optical element 10 and the wiring board 50 is filled with an underfill material, a sidefill material, or the like (not illustrated), as a sealing member. Alternatively, an electronic component 59 such as a chip condenser or an IC may be mounted on the second main surface 50SB of the wiring board 50.

A cutout N50 having a rectangular shape in plan view and having a short side length W50 equal to the width of the optical fiber 20A is formed in the wiring board 50. The end portion (a distal end and both side surfaces) of the optical fiber 20A is in contact with a wall surface (e.g., N50S) of the cutout N50 in the wiring board 50.

That is, as a result of contact of the cutout surface 20SB with the light emitting surface 10SA of the optical element 10 and contact of the end portion of the optical fiber 20A with the wall surface of the cutout N50 in the wiring board 50, positioning of the optical fiber 20A is automatically performed in the in-plane direction (the XY direction).

Since the cable 30 is not bonded to the optical element 10 in the optical transmission module 1D, the optical transmission module 1D can be more easily manufactured than the optical transmission module 1.

Second Embodiment

Next, an optical transmission module 1E of a second embodiment is described. The optical transmission module 1E is similar to the optical transmission module 1 and provides the same effect as the effect provided by the optical transmission module 1. Therefore, components having the same functions are denoted by the same reference numerals and an explanation thereof is omitted.

Figure 7:
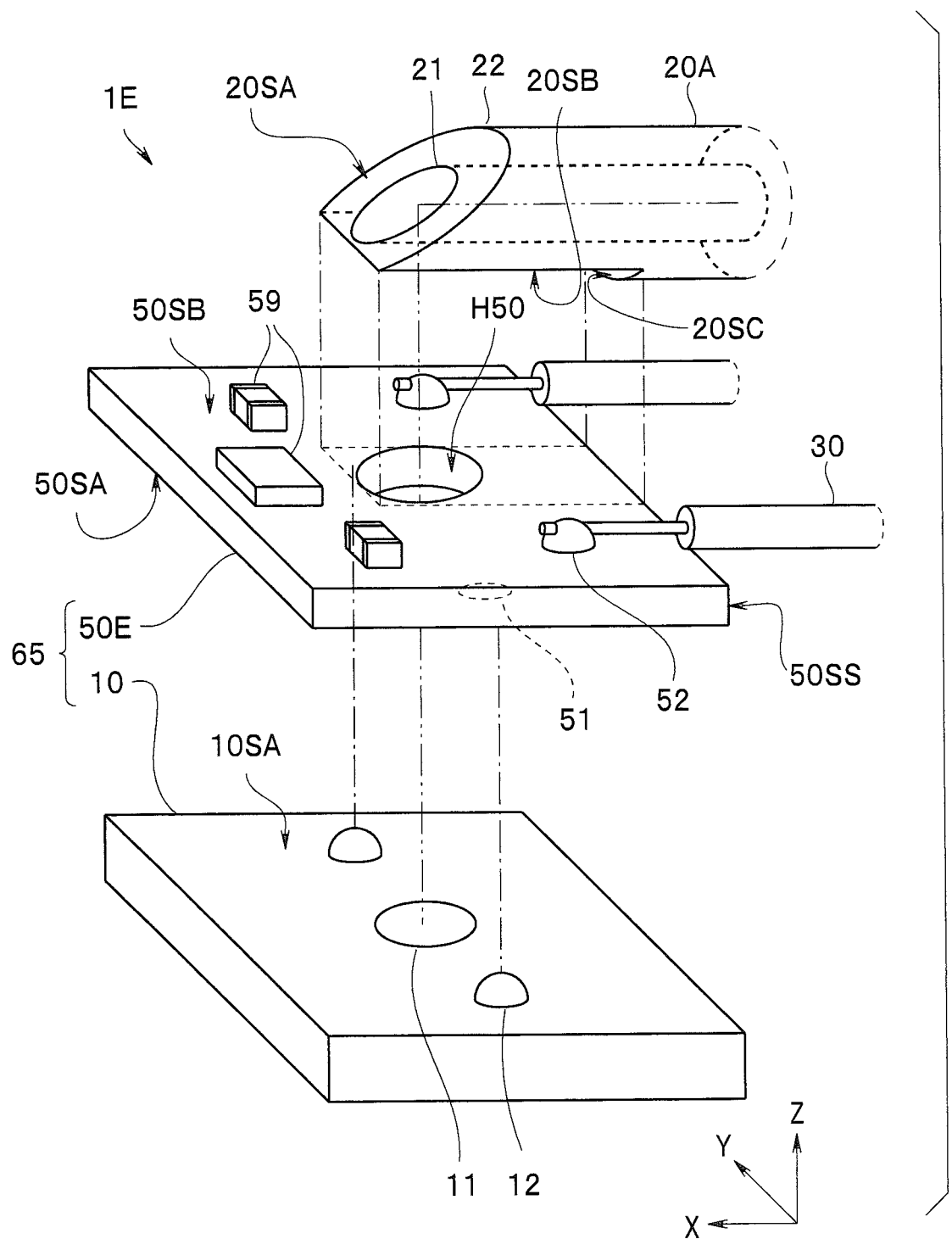
FIG. 7 is an exploded view of an optical transmission module of a second embodiment.

As illustrated in FIG. 7, an optical element part 65 of the optical transmission module 1E includes the optical element 10 and a wiring board 50E. The wiring board 50E includes the first main surface 50SA and the second main surface 50SB opposite to the first main surface 50SA.

The configuration of the wiring board 50E is substantially the same as the configuration of the wiring board 50 having been described above. The optical element 10 is mounted on the first main surface 50SA. However, the wiring board 50E differs from the wiring board 50 in that the wiring board 50E has a through hole H50 whereas the wiring board 50 has the cutout N50.

The through hole H50 serves as an optical path through which light emitted from the light emitting unit 11 passes. For example, the optical element 10 is mounted on the first main surface 50SA of the wiring board 50E in a state where the light emitting unit 11 of the optical element 10 is disposed at a position facing the through hole H50 in the wiring board 50E. The light emitting surface 10SA of the optical element 10 is disposed in parallel with the first main surface 50SA and the second main surface 50SB of the wiring board 50E.

The configuration of the optical fiber 20 of the optical transmission module 1E is the same as the configuration of the optical fiber 20 of the optical transmission module 1 so that the center line LC20 of the cutout surface 20SB intersects with the long axis L20 of the inclined surface 20SA (not illustrated).

In the optical transmission module 1E, the cutout surface 20SB of the optical fiber 20 is in contact with the second main surface 50SB of the wiring board 50E. Accordingly, the angle θ of the inclined surface 20SA with respect to the main surface 10SA of the optical element 10, that is, the rotation direction of the optical fiber 20 is automatically defined such that light guided through the optical fiber 20 is optically coupled to the optical element 10.

Note that, as a result of contact of the rear end wall surface 20SC of the cutout C20 with a rear side surface 50SS of the wiring board 50E, positioning of the optical fiber 20 is automatically performed in the in-plane direction.

Since the cable 30 is not bonded to the optical element 10 in the optical transmission module 1E, the optical transmission module 1E can be more easily manufactured than the optical transmission module 1.

Modifications of Second Embodiment

Next, optical transmission modules 1F to 1J of first to fourth modifications of the second embodiment are described. The optical transmission modules 1F to 1J are each similar to any one of the optical transmission modules 1 to 1E and provide the same effect as the effects provided by the optical transmission modules 1 to 1E. Therefore, components having the same functions are denoted by the same reference numerals and an explanation thereof is omitted.

As described above, in the optical transmission module 1E, positioning of the optical fiber 20 is defined in the in-plane direction (the XY direction) by the rear end wall surface 20SC of the cutout C20.

In contrast, in each of the optical transmission modules 1F to 1H, a positioning member with which the end portion of the optical fiber 20A is in contact is provided on the second main surface 50SB which is a wiring board arranged in parallel with the light emitting surface (the main surface) 10SA of the optical element 10.

First Modification of Second Embodiment

Figure 8:
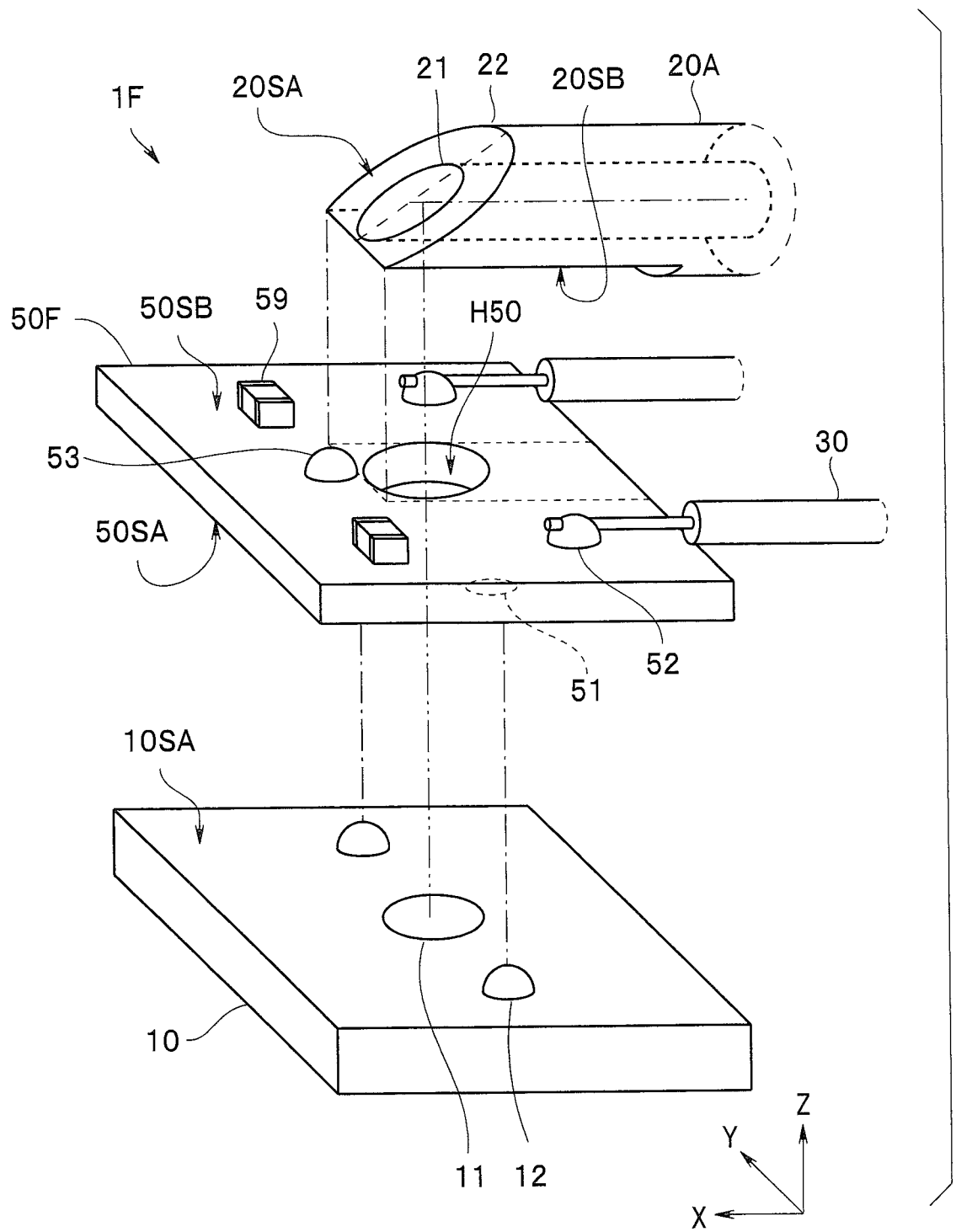
FIG. 8 is an exploded view of an optical transmission module of a first modification of the second embodiment.

As illustrated in FIG. 8, the optical transmission module 1F of the first modification of the second embodiment is similar to the optical transmission module 1A, in particular. That is, in the optical transmission module 1F, the positioning member is a third bump 53 provided on the second main surface of a wiring board 50F. That is, as a result of contact of the end portion of the optical fiber 20A with the third bump 53 on the wiring board 50F, the position of the optical fiber 20A is automatically defined in the optical axis direction (the X direction).

In the optical transmission module 1E, positioning of the optical fiber 20 is performed in the in-plane direction by means of the rear end wall surface 20SC of the cutout C20. However, there is a possibility that processing of a precise cutout in the optical fiber 20 is not easy.

Since the configuration of the third bump 53 which is a bump for positioning in the optical axis direction is the same as the configuration of the bonding bump 52, the third bump 53 can be provided simultaneously with the time of production of the wiring board 50E by the same process. Therefore, the optical transmission module 1F can be more easily manufactured than the optical transmission module 1E.

Second Modification of Second Embodiment

Figure 9:
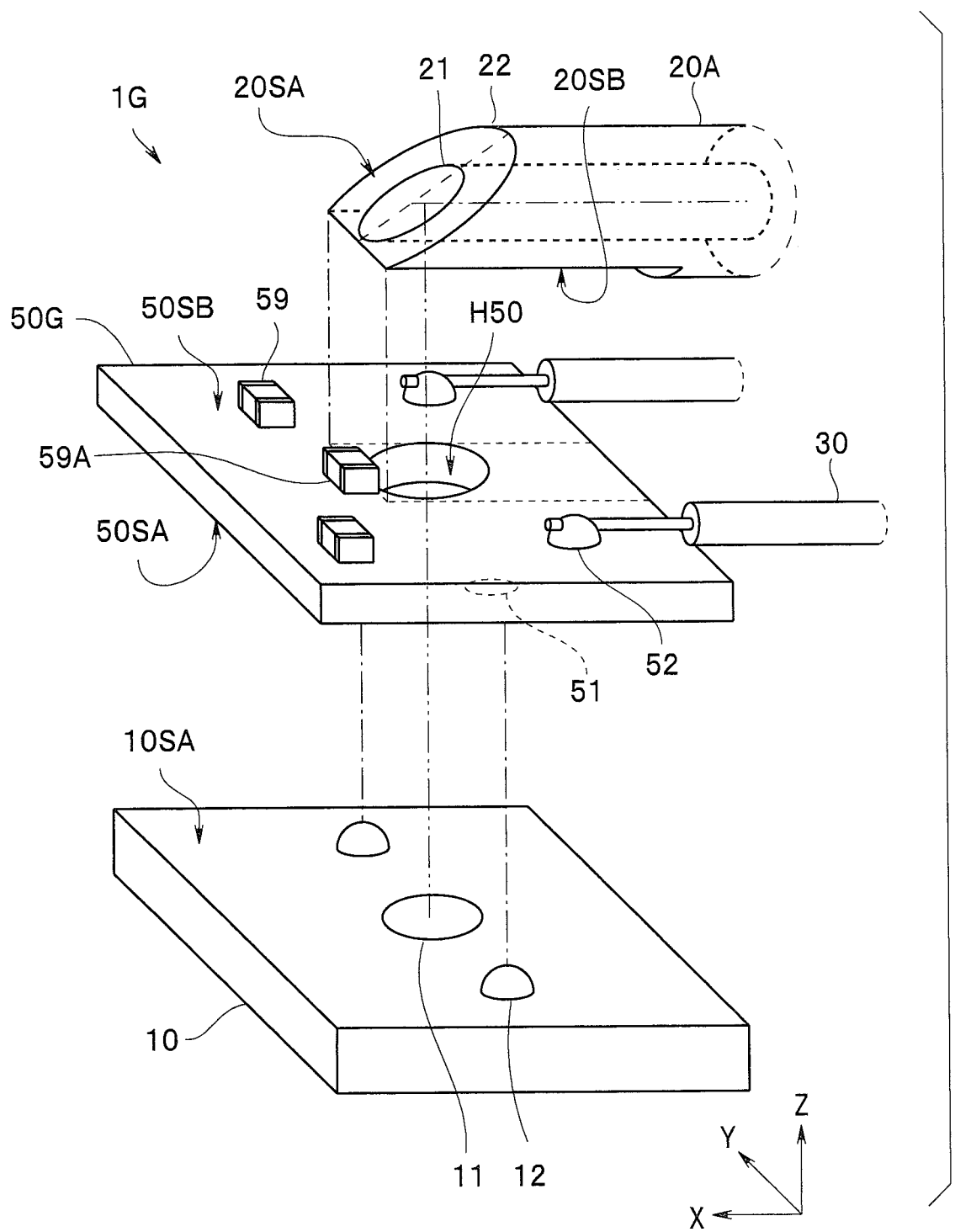
FIG. 9 is an exploded view of an optical transmission module of a second modification of the second embodiment.

As illustrated in FIG. 9, in the optical transmission module 1G of the second modification of the second embodiment, the positioning member is a first electronic component 59A which is a member for positioning in the optical axis direction and which is mounted on the second main surface 50SB of a wiring board 50G. As illustrated in FIG. 9, in the optical transmission module 1G, the end portion of the optical fiber 20A is arranged so as to be in contact with the first electronic component 59A, and the position of the optical fiber 20A can be automatically defined in the optical axis direction (the X direction).

The electronic components 59, 59A are bonded to an electrode pad provided at the time of production of the wiring board 50G. The electronic component 59A for electric circuit formation is an essential component for the optical transmission module 1G, and a function of the positioning member is added to the electronic component 59A. Note that the electronic component 59A has a necessary and sufficient height for positioning.

In the optical transmission module 1G, provision of the third bump 53 exclusively for positioning is unnecessary to the wiring board 50G. Since the area of the second main surface 50SB of the wiring board 50G can be made small, the diameter of the optical transmission module 1G is smaller than the diameter of the optical transmission module 1F.

Third Modification of Second Embodiment

Figure 10:
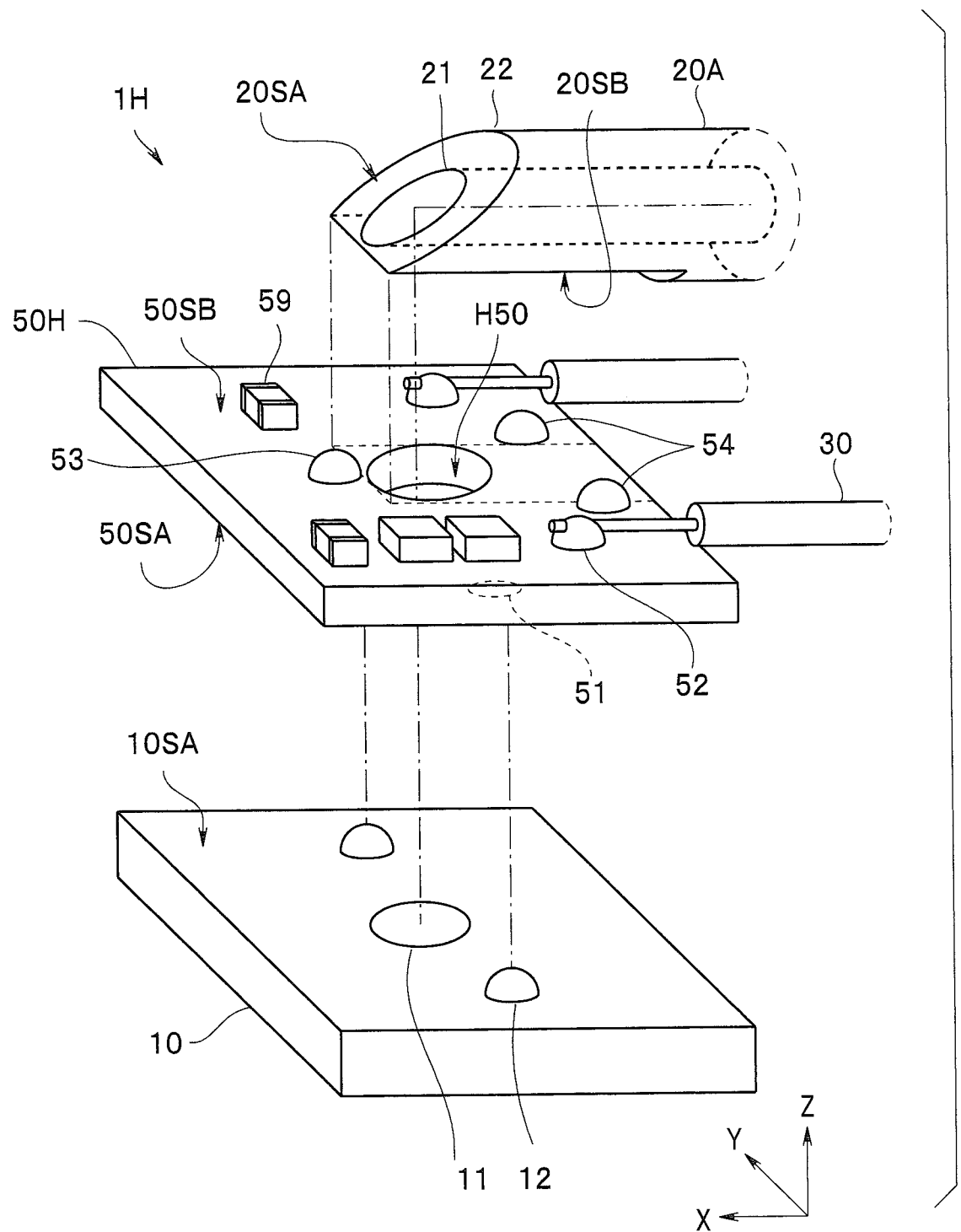
FIG. 10 is an exploded view of an optical transmission module of a third modification of the second embodiment.

As illustrated in FIG. 10, the optical transmission module 1H of the third modification of the second embodiment is similar to the optical transmission module 1B, in particular. That is, the optical transmission module 1H includes, on the second main surface 50SB of a wiring board 50H, a fourth bump 54 in contact with a side surface of the optical fiber 20A, in addition to the third bump 53.

The configuration of the fourth bump 54, which is a bump for positioning in the direction orthogonal to the optical axis, is substantially the same as the configuration of each of the bonding bump 52 and the third bump 53. That is, the fourth bump 54 can be provided simultaneously with the bonding bump 52 and the third bump 53 by the same process.

Positioning of the optical fiber 20A having a side surface in contact with the fourth bump 54 is automatically performed in the direction (the Y direction) orthogonal to the optical axis. Therefore, the optical transmission module 1H can be more easily manufactured than the optical transmission modules 1E and 1F.

Note that positioning of the optical fiber 20A can be automatically performed in the direction (the Y direction) orthogonal to the optical axis as long as one side surface of the optical fiber 20A is in contact with at least one fourth bump 54. However, in order to facilitate the positioning, the wiring board 50H preferably includes a plurality of the fourth bumps 54 in contact with both side surfaces of the optical fiber 20A.

Note that, even in a case (not illustrated) where a side surface of the optical fiber 20A is arranged so as to be in contact with a second electronic component which is a member for positioning in the direction orthogonal to the optical axis and which is mounted on the second main surface 50SB of the wiring board, the position of the optical fiber 20A can be automatically defined in the direction (the Y direction) orthogonal to the optical axis.

It is readily understood that, in the optical transmission module including the wiring board on which the first electronic component as a member for positioning in the optical axis direction and the second electronic component as a member for positioning in the direction orthogonal to the optical axis are disposed, the position of the optical fiber 20A can be automatically defined in the in-plane direction (the XY direction).

Fourth Modification of Second Embodiment

Figure 11:
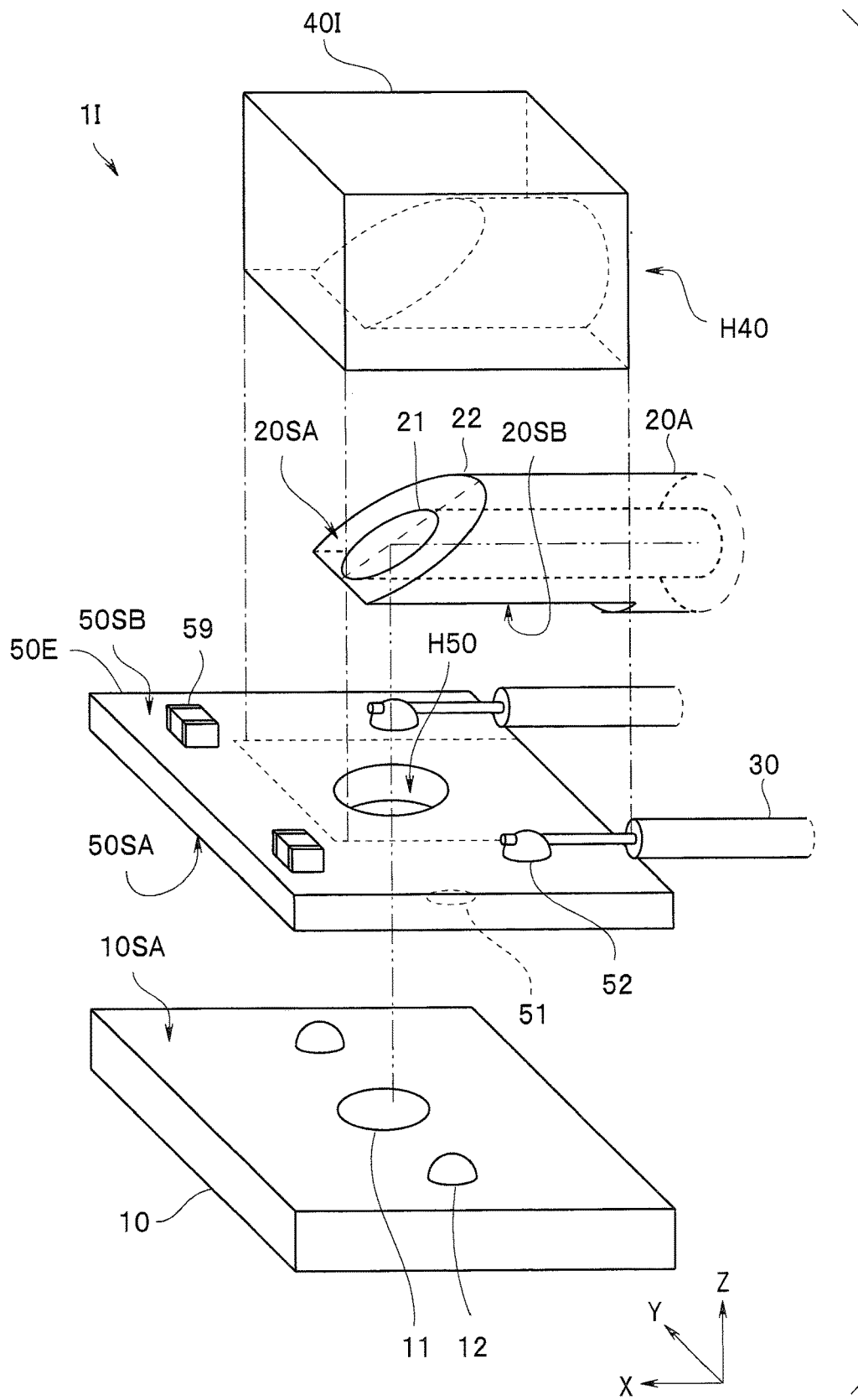
FIG. 11 is an exploded view of an optical transmission module of a fourth modification of the second embodiment.

As illustrated in FIG. 11, the optical transmission module 1I of the fourth modification of the second embodiment is similar to the optical transmission module 1C, in particular. That is, in the optical transmission module 1I, the recessed portion H40 in which the end portion of the optical fiber 20A is inserted and fitted is formed in a positioning member 40I provided on the second main surface of the wiring board 50E.

That is, the configuration of the positioning member 40I is substantially the same as the configuration of the positioning member 40.

As a result of contact of the cutout surface 20SB with the light emitting surface 10SA of the wiring board 50E and insertion and fitting of the end portion of the optical fiber 20A in the recessed portion H40 of the positioning member 40I, positioning of the optical fiber 20A can be automatically performed in the in-plane direction (the XY direction).

Therefore, the optical transmission module 1I can be more easily manufactured than the optical transmission module 1E.

Note that, as a positioning member for bonding the positioning member 40I to the wiring board 50E, a bump or an electronic component similar to any one of the bumps or the electronic components of the optical transmission modules 1F to 1H may be used.

Third Embodiment

An optical transmission module 1J of a third embodiment is described. The optical transmission module 1J is similar to the optical transmission module 1 and provides the same effect as the effect provided by the optical transmission module 1. Therefore, components having the same functions are denoted by the same reference numerals and an explanation thereof is omitted.

Figure 12:
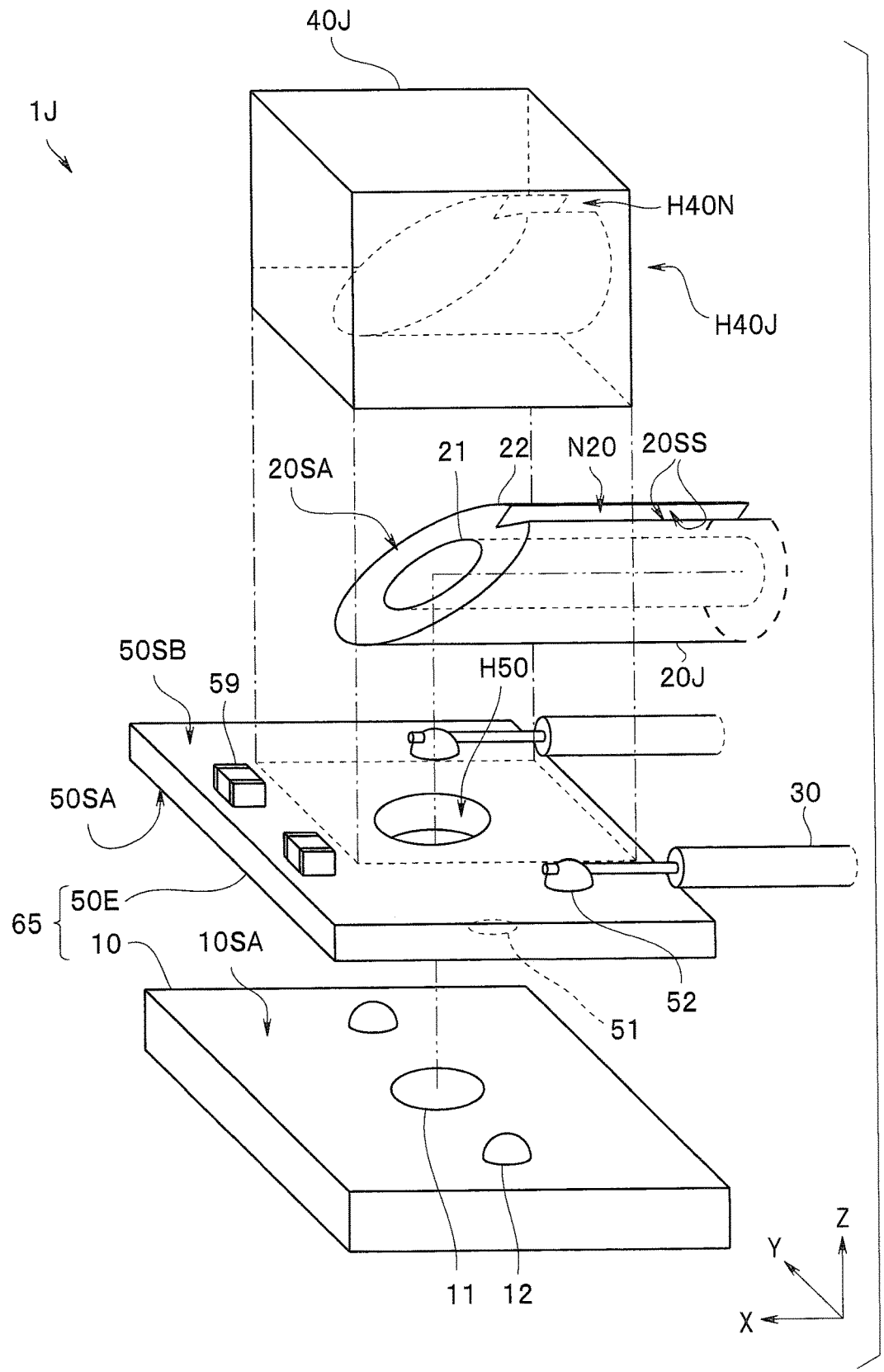
FIG. 12 is an exploded view of an optical transmission module of a third embodiment.
Figure 13:
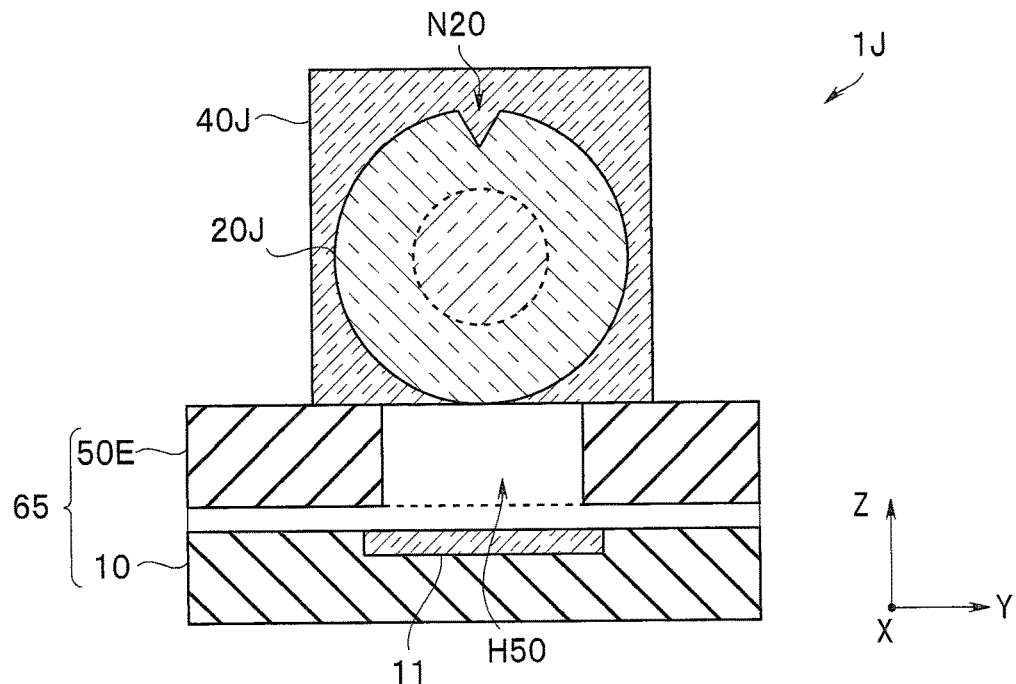
FIG. 13 is a cross-sectional view of the optical transmission module of the third embodiment.

As illustrated in FIG. 12 and FIG. 13, the optical element part 65 of the optical transmission module 1J includes the optical element 10 and the wiring board 50E.

In the optical transmission module 1J, the inclined surface 20SA of an optical fiber 20J is a wall surface of the groove N20 which is formed in the outer circumference and which extends in the optical axis direction. In other words, the groove N20 in the optical fiber 20J has two rectangular cutout surfaces 20SS extending in the optical axis. The groove N20 is formed in the clad 22 and does not reach the core 21.

The optical element part 65 includes the wiring board 50E having the first main surface 50SA, on which the optical element 10 is mounted, and the second main surface 50SB. The positioning member 40J including a recessed portion H40J that has a projection portion H40N on the inner wall surface of the recessed portion H40J is provided on the first main surface 50SA of the wiring board 50E.

The positioning member 40J is preferably made from a transparent resin having a refractive index equal to the refractive index of the clad 22 of the optical fiber 20J. Further, an area between the recessed portion H40J of the positioning member 40J and the outer surface of the optical fiber 20J is preferably filled with a transparent resin having a refractive index equal to the refractive index of the clad 22.

The optical fiber 20J is fitted to the recessed portion H40J of the positioning member 40J. That is, the groove N20 in the optical fiber 20J is fitted to the projection portion H40N on the recessed portion H40J of the positioning member 40J.

As a result of contact of the two cutout surfaces 20SS of the groove N20 in the optical fiber 20J with both wall surfaces of the projection portion H40N of the positioning member 40J, the angle (the rotation direction) of the inclined surface 20SA of the optical fiber 20J with respect to the light emitting surface 10SA of the optical element 10 is automatically defined such that light guided through the optical fiber 20J is optically coupled to the optical element 10, and positioning of the optical fiber 20J is automatically performed in the in-plane direction (the XY direction), whereby the optical fiber 20J is fixed.

Note that the recessed portion H40J may have a cylindrical shape with a circular distal end surface or may be a through hole, as long as the wall surface of the recessed portion H40J is fitted to the outer circumferential surface of the optical fiber 20J. In addition, although the groove N20 is formed in the upper surface of the optical fiber 20J in the optical transmission module 1J illustrated in FIG. 12, the groove N20 may be formed in a lateral surface, etc. other than the lower surface as long as the bottom of the groove N20 does not reach the core 21.

Figure 14A:
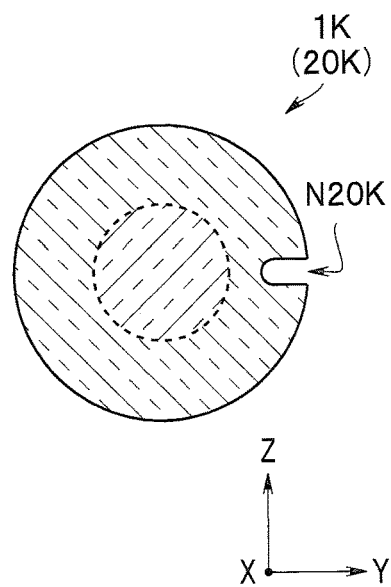
FIG. 14A is a cross-sectional view of an optical fiber of an optical transmission module of a first modification of the third embodiment.
Figure 14B:
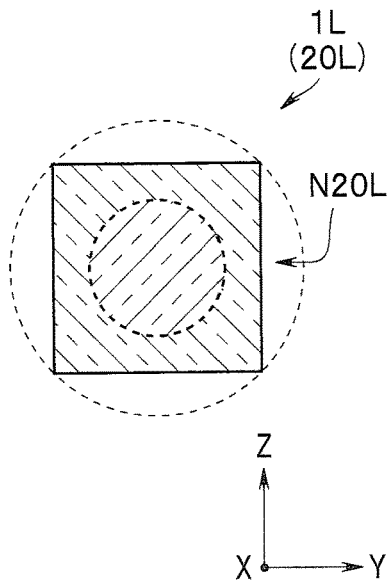
FIG. 14B is a cross-sectional view of an optical fiber of an optical transmission module of a second modification of the third embodiment.

Note that, as illustrated in FIG. 14A, in an optical transmission module 1K, a groove N20K in an optical fiber 20K has a U-like cross section. And as illustrated in FIG. 14B, in an optical transmission module 1L, an optical fiber 20L has a rectangular cross section or, in other words, has a groove N20L in a side surface of the optical fiber 20L.

Each of the optical transmission modules 1K and 1L has, in the outer circumference of an end portion of the optical fiber, a cutout surface extending in the optical axis and has a positioning member including a hole with a projection portion such that the cutout surface of the optical fiber is fitted to the projection portion, and thereby, provides the same effect as the effect provided by the optical transmission module 1J.

The outer circumference portion of the optical fiber 20 is exposed from the lower surface of the positioning member 40J. However, the optical fiber 20L may be inserted in the through hole. To make the optical path length short, the shorter length of the lower surface of the positioning member 40J is more preferable.

Fourth Embodiment

Next, an endoscope 9 of a fourth embodiment is described.

Figure 15:
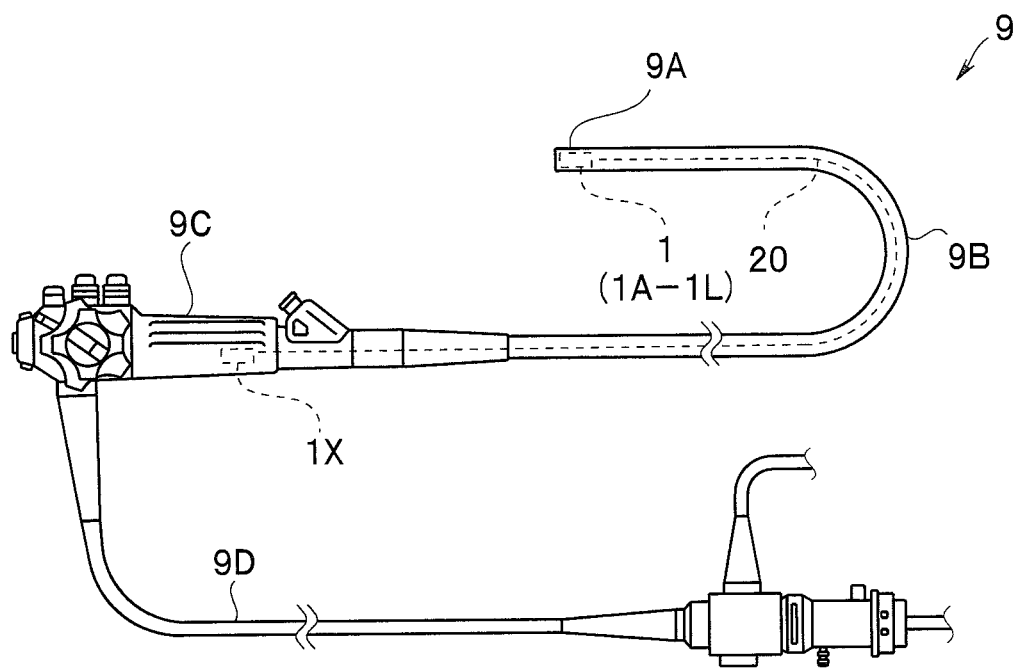
FIG. 15 is a perspective view of an endoscope of a fourth embodiment.

As illustrated in FIG. 15, the endoscope 9 includes an insertion section 9B having a rigid distal end portion 9A provided with any one of the optical transmission modules 1 to 1L, an operation section 9C provided at the proximal end side of the insertion section 9B, and a universal cord 9D extending from the operation section 9C. Note that an optical signal outputted from the one of the optical transmission modules 1 to 1L provided in the rigid distal end portion 9A and guided through the optical fiber 20 inserted in the insertion section 9B is converted to an electrical signal by an optical transmission module 1X that is provided in the operation section 9C, for example.

The endoscope 9 includes any one of the optical transmission modules 1 to 1L each having a small diameter, and accordingly, the rigid distal end portion 9A has a small diameter. In addition, since the endoscope 9 includes any one of the optical transmission modules 1 to 1L, the endoscope 9 can be easily manufactured.

The present invention is not limited to the embodiments and the modifications which have been described above, and various modifications, various combinations, and various applications of the embodiments and the modifications can be made within the scope of the gist of the invention.

What is claimed is:

1. An optical transmission module, comprising:
an optical fiber having a circular cross section, the optical fiber having an inclined end surface;
an optical element having a main surface, the main surface having one of a light emitting element having a light emitting surface on the main surface or a light receiving element having a light receiving surface on the main surface; and
a wiring board including a first main surface on which the optical element is mounted, the wiring board including a second main surface opposite to the first main surface, and the wiring board including a through hole serving as an optical path;
wherein
a cutout surface extending in an optical axis direction is formed in an outer circumference of an end portion of the optical fiber,
an angle of the inclined end surface with respect to the main surface of the optical element is defined by the cutout surface, such that light guided through the optical fiber is optically coupled to the optical element;

a center line of the cutout surface of the optical fiber intersects with the longitudinal axis of the inclined end surface, and the cutout surface is in contact with the second main surface of the wiring board.

2. The optical transmission module according to claim 1, wherein the cutout surface of the optical fiber has a rectangular shape.

3. The optical transmission module according to claim 2, wherein the outer circumference of the end portion of the optical fiber includes a rear end wall surface perpendicular to the cutout surface, and the rear end wall surface contacts with a rear side surface of the wiring board such that a position of the optical fiber with respect to the wiring board is defined in an in-plane direction.

4. The optical transmission module according to claim 1, further comprising a positioning member in contact with the end portion of the optical fiber, the positioning member being provided on the second main surface of the wiring board.

5. The optical transmission module according to claim 4, wherein the positioning member is a first bump.

6. The optical transmission module according to claim 5, further comprising a second bump provided on the second main surface of the wiring board, the second bump being in contact with a side surface of the optical fiber.

7. The optical transmission module according to claim 4, wherein the positioning member includes a recessed portion, the end portion of the optical fiber being inserted and fitted in the recessed portion.

8. The optical transmission module according to claim 4, wherein the positioning member comprises a cutout formed in the wiring board, the cutout having a rectangular shape in plan view and having a shorter side, a length of the shorter side being equal to a width of the optical fiber, and the end portion of the optical fiber is in contact with a wall surface of the cutout in the wiring board.

9. The optical transmission module according to claim 1, wherein the outer circumference of the end portion of the optical fiber includes a rear end wall surface perpendicular to the cutout surface, and the rear end wall surface contacts with a rear side surface of the wiring board such that a position of the optical fiber with respect to the optical element is defined in an in-plane direction.

10. The optical transmission module according to claim 4, wherein the positioning member comprises one of a third bump or a first electronic component.

11. The optical transmission module according to claim 10, wherein the positioning member comprises one of a fourth bump or a second electronic component on the second main surface of the wiring board, the fourth bump or the second electronic component being in contact with a side surface of the optical fiber.

12. An endoscope comprising:
an insertion section having a rigid distal end portion; and
the optical transmission module according to claim 1 disposed at the rigid distal end portion of the insertion section.

* * * * *